United States Patent
Oka et al.

(10) Patent No.: US 9,308,291 B2
(45) Date of Patent: Apr. 12, 2016

(54) MEDICAL PRESSURE-SENSITIVE ADHESIVE SHEET AND METHOD FOR PRODUCING THE SAME

(71) Applicant: PIAC CO., LTD., Shiga (JP)

(72) Inventors: Keiji Oka, Shiga (JP); Junji Fukushima, Shiga (JP)

(73) Assignee: PIAC CO., LTD., Shiga (JP)

( * ) Notice: Subject to any disclaimer, the term of this patent is extended or adjusted under 35 U.S.C. 154(b) by 0 days.

(21) Appl. No.: 14/403,244

(22) PCT Filed: Oct. 29, 2013

(86) PCT No.: PCT/JP2013/079184
§ 371 (c)(1),
(2) Date: Nov. 24, 2014

(87) PCT Pub. No.: WO2014/132488
PCT Pub. Date: Sep. 4, 2014

(65) Prior Publication Data
US 2015/0093557 A1    Apr. 2, 2015

(30) Foreign Application Priority Data

Mar. 1, 2013   (JP) .................. 2013-040707

(51) Int. Cl.
*A61L 15/58*       (2006.01)
*B32B 37/15*       (2006.01)
(Continued)

(52) U.S. Cl.
CPC ............. *A61L 15/58* (2013.01); *A61F 13/0246* (2013.01); *A61F 13/0276* (2013.01); *A61L 15/24* (2013.01);
(Continued)

(58) Field of Classification Search
CPC .......... A61L 15/58; A61L 15/42; B32B 37/15
USPC ............................. 428/214; 156/60
See application file for complete search history.

(56) References Cited

U.S. PATENT DOCUMENTS

| | | | |
|---|---|---|---|
| 5,633,070 | A | 5/1997 | Murayama et al. |
| 2005/0031860 | A1 | 2/2005 | Okada et al. |

(Continued)

FOREIGN PATENT DOCUMENTS

| | | |
|---|---|---|
| JP | 8-33673 A | 2/1996 |
| JP | 2003-250879 A | 9/2003 |

(Continued)

OTHER PUBLICATIONS

Machine_English_Translation_JP_2008007930_A; Shimizu, Hiroyasu; Stretchable Nonwoven Fabric; Jan. 17, 2008; JPO; whole document.*

*Primary Examiner* — Tahseen N Khan
(74) *Attorney, Agent, or Firm* — Fitch, Even, Tabin & Flannery LLP

(57) ABSTRACT

A medical pressure-sensitive adhesive sheet includes a urethane substrate, an interlayer adhesive layer, an olefin nonwoven fabric, and a pressure-sensitive adhesive layer for pasting in order and has a moisture permeability amount of 2000 $g/(m^2 \cdot 24$ hours) or more, or the like. In the medical pressure-sensitive adhesive sheet, a thickness of the urethane substrate is a value within the range of from 1 to 10 μm, a thickness of the interlayer adhesive layer is a value within the range of from 5 to 30 μm, the olefin nonwoven fabric is constituted with a polypropylene-based thermoplastic elastomer and has a maximum point elongation percentage of a value of 200% or more in the longitudinal direction and the transverse direction, respectively, and a thickness of the pressure-sensitive adhesive layer for pasting is a value within the range of from 5 to 45 μm.

10 Claims, 6 Drawing Sheets

(51) Int. Cl.

| | | |
|---|---|---|
| *A61L 15/42* | (2006.01) | |
| *A61F 13/02* | (2006.01) | |
| *A61L 15/24* | (2006.01) | |
| *C08L 35/04* | (2006.01) | |
| *B32B 27/00* | (2006.01) | |
| *B32B 37/12* | (2006.01) | |
| *B32B 5/02* | (2006.01) | |
| *B32B 7/06* | (2006.01) | |
| *B32B 7/12* | (2006.01) | |
| *B32B 27/12* | (2006.01) | |
| *B32B 27/40* | (2006.01) | |
| *B32B 38/00* | (2006.01) | |
| *C09J 133/14* | (2006.01) | |
| *C08L 23/10* | (2006.01) | |

(52) U.S. Cl.
CPC ............... *A61L 15/42* (2013.01); *B32B 5/022* (2013.01); *B32B 7/06* (2013.01); *B32B 7/12* (2013.01); *B32B 27/00* (2013.01); *B32B 27/12* (2013.01); *B32B 27/40* (2013.01); *B32B 37/12* (2013.01); *B32B 37/15* (2013.01); *C08L 35/04* (2013.01); *B32B 38/0004* (2013.01); *B32B 2037/1253* (2013.01); *B32B 2274/00* (2013.01); *B32B 2307/726* (2013.01); *B32B 2307/748* (2013.01); *B32B 2375/00* (2013.01); *B32B 2535/00* (2013.01); *B32B 2556/00* (2013.01); *C08L 23/10* (2013.01); *C09J 133/14* (2013.01); *Y10T 156/10* (2015.01); *Y10T 428/24959* (2015.01)

(56) References Cited

U.S. PATENT DOCUMENTS

| | | |
|---|---|---|
| 2009/0054821 A1 | 2/2009 | Tanaka et al. |
| 2010/0282269 A1 | 11/2010 | Uchida et al. |
| 2011/0098622 A1* | 4/2011 | Hatanaka et al. ............... 602/52 |

FOREIGN PATENT DOCUMENTS

| | | | |
|---|---|---|---|
| JP | 2005-58341 A | | 3/2005 |
| JP | 2008-7930 A | | 1/2008 |
| JP | 2008007930 A | * | 1/2008 |
| JP | 4139482 B2 | | 6/2008 |
| JP | 4755284 B2 | | 6/2011 |
| WO | 2007/114295 A1 | | 10/2007 |

* cited by examiner

MEDICAL PRESSURE-SENSITIVE ADHESIVE SHEET AND METHOD FOR PRODUCING THE SAME

BACKGROUND OF THE INVENTION

1. Field of the Invention

The present invention relates to a medical pressure-sensitive adhesive sheet and a method for producing the same. In particular, it relates to a medical pressure-sensitive adhesive sheet excellent in elasticity, handling or the like while maintaining excellent moisture permeability or water resistance and a method for producing such a medical pressure-sensitive adhesive sheet.

2. Description of the Related Art

Hitherto, various kinds of medical pressure-sensitive adhesive sheets have been proposed which exhibit excellent moisture permeability or elasticity and also favorable water proofing property or the like.

For example, a pressure-sensitive adhesive film for first-aid adhesive plaster has been proposed in which skin irritation due to the occurrence of sweatiness is prevented without inhibiting the cutaneous respiration (for example, see JP 8-33673 A (claims or the like)).

More specifically, as illustrated in FIG. 6B, it is a pressure-sensitive adhesive film for first-aid adhesive plaster 100 formed by pattern coating one surface of a nonwoven fabric 101 composed of a SIS block copolymer or the like with a porous pressure-sensitive adhesive 102. In the pressure-sensitive adhesive film for first-aid adhesive plaster 100, another substrate 106 such as a polyurethane film is thermally laminated on the surface of the nonwoven fabric 101 which is the side opposite to the surface coated with the pressure-sensitive adhesive 102, and further an edge portion 105 is sealed.

Meanwhile, as illustrated in FIG. 6A, it is a pressure-sensitive adhesive film for first-aid adhesive plaster 100 in which a pad 104 is provided at a predetermined place of the pressure-sensitive adhesive 102 and two release sheets 103 are layered so as to conceal the pressure-sensitive adhesive 102 including the pad 104.

In addition, an electron beam resistant medical covering material has been proposed which exhibits sufficient flexibility, excellent strength, and electron beam resistance as well as moisture permeability and water proofing property (for example, see JP 4,139,482 B1 (claims or the like)).

More specifically, it is an electron beam resistant medical covering material which has a three-layer structure and is formed by thermally laminating a nonwoven fabric sheet containing an ethylene • α-olefin copolymer on both sides of a substrate such as a polyether block amide copolymer film having a water bearing pressure of 2000 mm $H_2O$ or more and a moisture permeability amount of 1500 $g/m^2 \cdot 24$ hours or more.

In addition, a medical sheet consisting of a predetermined polyurethane nonwoven fabric/hot melt type adhesive/polyurethane film and a method for producing the same have been proposed for the purpose to improve elasticity, breathability, moisture permeability, water proofing property or the like (for example, see WO 2007-114295 (claims or the like)).

More specifically, it is a medical sheet formed by thermally laminating a polyurethane nonwoven fabric formed from a fiber having an average fiber diameter of 50 μm or less by the melt blow method and a polyurethane film having micropores (through holes) with a diameter of 10 μm or less formed on both sides thereof using the phase separation phenomenon via a pattern coated hot melt type adhesive.

In addition, an elastic nonwoven fabric has been proposed which is used in a medical material or the like and exhibits sufficient strength or favorable sticking property (anti-blocking property) as well as excellent elasticity and flexibility (for example, see JP 2008-7930 A (claims or the like)).

More specifically, it is an elastic nonwoven fabric formed by melt spinning a mixture (mixing weight ratio=50/50 to 95/5) of a thermoplastic elastomer component (A) such as an elastomeric polypropylene having an MFR value of 50 to 400 g/10 minutes and a polypropylene resin (B) having an MFR value of 25 to 200 g/10 minutes.

Moreover, a pasting material has been proposed which is excellent in pasting ability to the human skin and consists of a predetermined polyurethane elastomer film and a predetermined pressure-sensitive adhesive layer (for example, see JP 4,755,284 B1 (claims or the like).

More specifically, it is a pasting material which has a layer structure in which a pressure-sensitive adhesive layer is provided on one surface of the substrate layer and satisfies the following features (a) to (f).

(a) The substrate layer is a polyurethane elastomer film having a thickness within the range of from 1 to 8 μm.

(b) The thickness of the pressure-sensitive adhesive layer is within the range of from 1 to 10 μm.

(c) The total thickness of the substrate layer and the pressure-sensitive adhesive layer is within the range of from 2 to 15 μm.

(d) The 10% tensile load of the pasting material measured in conformity with JIS Z 0237 of the Japanese Industrial Standards is within the range of from 0.03 to 1.1 N/10 mm in each of the longitudinal and transverse directions.

(e) The product XY value of the 10% tensile load value X and the thickness value Y of the pasting material is within the range of from 0.1 to 12 or the product XZ value of the 10% tensile load value X and the thickness value Z of the substrate layer is within the range of from 0.05 to 6.8 when the 10% tensile load value of the pasting material in the longitudinal direction is denoted as X (N/10 mm), the thickness value of the pasting material is denoted as Y (μm), and the thickness value of the substrate layer is denoted as Z (μm).

(f) The pressure-sensitive adhesive layer exhibits an adhesive force of from 0.15 to 2 N/10 mm in the 90° peeling test of a pair of bakelite plates defined in JIS Z 0237.

SUMMARY OF THE INVENTION

However, there has been observed a problem in the pressure-sensitive adhesive film for first-aid adhesive plaster disclosed in JP 8-33673 A (claims or the like) that a special waterproofing treatment of sealing of the edge portion is an essential and thus the manufacturing cost increases or the manufacturing processes are likely to increase.

In addition, there has been observed a problem that handling is excessively difficult in a case in which the substrate such as a polyurethane film is ultrathin to be 10 μm or less and thus it is not possible to accurately paste the pressure-sensitive adhesive film for first-aid adhesive plaster at a predetermined position.

Moreover, there has been also observed a problem that the manufacturing cost of the pressure-sensitive adhesive film for first-aid adhesive plaster further increases or the elasticity or water vapor permeability excessively deteriorates in the case of using a nonwoven fabric composed of a SIS block copolymer or the like.

In addition, the electron beam resistant medical covering material disclosed in JP 4,139,482 B1 (claims or the like) has an excellent moisture permeability amount, but there has been observed a problem that the covering material needs to be configured by a three-layer structure using a substrate such as an expensive polyether block amide copolymer film and thus the manufacturing cost increases or the elasticity significantly deteriorates since it becomes thick.

Moreover, there has been also observed a problem that peeling easily occurs between the substrate such as a polyether block amide copolymer film and the nonwoven fabric sheet composed of an ethylene • α-olefin copolymer or the like.

In addition, there has been observed a problem in the medical sheet consisting of a predetermined polyurethane nonwoven fabric/hot melt type adhesive/polyurethane film disclosed in WO 2007-114295 (claims or the like) that the manufacturing cost tends to increase since it needs to use a predetermined polyurethane nonwoven fabric.

Moreover, there has been observed a problem that the formation and control of the micropores on the polyurethane film are not easy and thus the moisture permeability amount and mechanical strength decrease, or the medical sheet is poor in heat resistance since a hot melt type adhesive is used.

In addition, there has been observed a problem in the elastic nonwoven fabric disclosed in JP 2008-7930 A (claims or the like) that the control of elasticity or moisture permeability amount is difficult since it needs to use a mixture of a thermoplastic elastomer having a predetermined fluidity such as elastomeric polypropylene and a homopolypropylene resin having a predetermined fluidity at a predetermined mixing ratio.

Moreover, there has been also observed a problem that peeling easily occurs when the elastic nonwoven fabric and a polyurethane film are thermally laminated.

Furthermore, there has been observed a problem in the pasting material disclosed in JP 4,755,284 B1 (claims or the like) that an ultrathin pressure-sensitive adhesive layer is directly formed with respect to an ultrathin polyurethane elastomer film and thus it is difficult to handle the pasting material and to accurately and quickly paste it at a predetermined place.

Moreover, there has been also observed a problem that the management of the manufacturing process is difficult or the manufacturing cost increases since it needs to satisfy all of the features (a) to (f).

In view of such circumstance, the present inventors have found out that elasticity, handleability or the like is significantly improved by forming a medical pressure-sensitive adhesive sheet consisting of an ultrathin urethane substrate, an interlayer adhesive layer, a predetermined olefin nonwoven fabric, and a pressure-sensitive adhesive layer for pasting without using a predetermined polyurethane nonwoven fabric or a porous urethane substrate, thereby the invention has been completed.

In other words, an object of the invention is to provide a medical pressure-sensitive adhesive sheet exhibiting excellent elasticity, handleability or the like while maintaining excellent moisture permeability or water resistance and a method for efficiently producing such a medical pressure-sensitive adhesive sheet.

According to the invention, a medical pressure-sensitive adhesive sheet is provided which includes a urethane substrate, an interlayer adhesive layer, an olefin nonwoven fabric, and a pressure-sensitive adhesive layer for pasting in order and has a moisture permeability amount of 2000 g/(m$^2$·24 hours) or more. In the medical pressure-sensitive adhesive sheet, the thickness of the urethane substrate is a value within the range of from 1 to 10 μm, the thickness of the interlayer adhesive layer is a value within the range of from 5 to 30 μm, the olefin nonwoven fabric is constituted with a polypropylene-based thermoplastic elastomer and has a maximum point elongation percentage of a value of 200% or more in the longitudinal direction and the transverse direction, respectively, and the thickness of the pressure-sensitive adhesive layer for pasting is a value within the range of from 5 to 45 μm. Hence, it is possible to solve the problem described above.

In other words, the thickness of the urethane substrate is ultrathin (1 to 10 μm) and thus favorable elasticity can be obtained while maintaining excellent moisture permeability or water resistance even when the medical pressure-sensitive adhesive sheet is a nonporous film.

In addition, an interlayer adhesive layer having a predetermined thickness is provided between the urethane substrate and the olefin nonwoven fabric, and thus favorable elasticity can be obtained while maintaining excellent moisture permeability (moisture permeability amount of 2000 g/(m$^2$·24 hours) or more) or water resistance in the entire medical pressure-sensitive adhesive sheet as well as favorable adhesiveness is obtained between the urethane substrate and the olefin nonwoven fabric.

Moreover, the olefin nonwoven fabric is constituted with a predetermined thermoplastic elastomer and has a maximum point elongation percentage of an equal to or more than a predetermined value in the longitudinal and transverse directions and thus favorable elasticity can be obtained while maintaining excellent moisture permeability or water resistance in the entire medical pressure-sensitive adhesive sheet.

Furthermore, the thickness of the interlayer adhesive layer between the layers and the thickness of the pressure-sensitive adhesive layer for pasting are relatively thin and thus favorable adhesive properties can be exhibited while maintaining excellent moisture permeability or elasticity in the entire medical pressure-sensitive adhesive sheet.

In addition, upon constituting the medical pressure-sensitive adhesive sheet of the invention, it is preferable that the content of the polypropylene-based thermoplastic elastomer contained in the olefin nonwoven fabric is a value of above 95% by weight with respect to a total amount of the olefin nonwoven fabric.

According to such a constitution, the deterioration in the elasticity of the olefin nonwoven fabric is suppressed and thus it is possible to maintain favorable elasticity or flexibility of the entire medical pressure-sensitive adhesive sheet.

Moreover, the adhesiveness with the urethane substrate by the interlayer adhesive layer is further improved by controlling the content of the polypropylene-based thermoplastic elastomer at the numerical value within such a range.

In addition, upon constituting the medical pressure-sensitive adhesive sheet of the invention, it is preferable that the MFR of the polypropylene-based thermoplastic elastomer contained in the olefin nonwoven fabric is a value within the range of from 1 to 48 g/10 minutes (temperature: 230° C.)

According to such a constitution, the deterioration in the elasticity of the olefin nonwoven fabric is suppressed although the productivity slightly deteriorates and thus it is possible to maintain favorable elasticity or flexibility or mechanical strength of the entire medical pressure-sensitive adhesive sheet.

In addition, upon constituting the medical pressure-sensitive adhesive sheet of the invention, it is preferable that the mass per unit area of the olefin nonwoven fabric is a value within the range of from 10 to 100 g/m$^2$.

According to such a constitution, the deterioration in the elasticity of the olefin nonwoven fabric is suppressed and thus it is possible to maintain favorable handleability, elasticity, and further flexibility of the entire medical pressure-sensitive adhesive sheet.

Moreover, the adhesiveness with the urethane substrate by the interlayer adhesive layer is further improved by controlling the mass per unit area of the olefin nonwoven fabric at the numerical value within such a range.

In addition, upon constituting the medical pressure-sensitive adhesive sheet of the invention, it is preferable that the 100% modulus of the olefin nonwoven fabric is a value within the range of from 2 to 30 N/50 mm.

According to such a constitution, the deterioration in the elasticity of the olefin nonwoven fabric is suppressed and thus it is possible to maintain favorable elasticity or flexibility or mechanical strength of the entire medical pressure-sensitive adhesive sheet.

In addition, upon constituting the medical pressure-sensitive adhesive sheet of the invention, it is preferable that the 100% modulus of the urethane/olefin composite substrate consisting of the urethane substrate/interlayer adhesive layer/olefin nonwoven fabric is a value within the range of from 3 to 30 N/50 mm.

According to such a constitution, it is possible to maintain favorable elasticity or flexibility or mechanical strength of the entire medical pressure-sensitive adhesive sheet.

In addition, upon constituting the medical pressure-sensitive adhesive sheet of the invention, it is preferable that the peel strength between the urethane substrate and the olefin nonwoven fabric is a value within the range of from 2 to 20 N/50 mm.

According to such a constitution, it is possible to maintain favorable elasticity or flexibility or mechanical strength of the entire medical pressure-sensitive adhesive sheet.

In addition, another aspect of the invention is a method for producing a medical pressure-sensitive adhesive sheet including a urethane substrate having a thickness of from 1 to 10 μm, an interlayer adhesive layer having a thickness of from 5 to 30 μm, an olefin nonwoven fabric constituted with a polypropylene-based thermoplastic elastomer and having a maximum point elongation percentage of a value of 200% or more in a longitudinal direction and a transverse direction, respectively, and a pressure-sensitive adhesive layer for pasting having a thickness of from 5 to 45 μm in order and having a moisture permeability amount of 2000 g/(m²·24 hours) or more, the method including the following processes (1) and (2):

(1) a process of layering the urethane substrate and the olefin nonwoven fabric via the interlayer adhesive layer to form a urethane/olefin composite substrate; and (2) a process of forming the pressure-sensitive adhesive layer for pasting with respect to the urethane/olefin composite substrate.

In other words, a urethane substrate having an ultrathin (1 to 10 μm) thickness is used and thus it is possible to obtain a medical pressure-sensitive adhesive sheet exhibiting favorable elasticity or flexibility at a low cost while maintaining excellent moisture permeability or water resistance although it is a nonporous film.

In addition, an interlayer adhesive layer having a predetermined thickness is provided between the urethane substrate and the olefin nonwoven fabric, and thus it is possible to obtain a medical pressure-sensitive adhesive sheet exhibiting favorable elasticity or flexibility while maintaining excellent moisture permeability or water resistance as well as excellent adhesiveness is obtained between the urethane substrate and the olefin nonwoven fabric.

Moreover, the olefin nonwoven fabric is constituted with a predetermined thermoplastic elastomer and has a maximum point elongation percentage of an equal to or more than a predetermined value in the longitudinal and transverse directions and thus it is possible to obtain a medical pressure-sensitive adhesive sheet exhibiting favorable elasticity or flexibility while maintaining excellent moisture permeability or water resistance.

Furthermore, the thickness of the pressure-sensitive adhesive layer for pasting is relatively thin and thus it is possible to obtain a medical pressure-sensitive adhesive sheet exhibiting favorable adhesive properties at a low cost while maintaining excellent moisture permeability or elasticity.

DETAILED DESCRIPTION OF THE PREFERRED EMBODIMENTS

[First Embodiment]

Figure 1A:
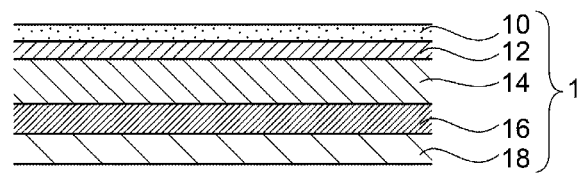
FIGS. 1A to 1D are diagrams presented to illustrate various aspects of a medical pressure-sensitive adhesive sheet.

As illustrated in FIG. 1A, the first embodiment is a medical pressure-sensitive adhesive sheet 1 which includes a urethane substrate 10, an interlayer adhesive layer 12, an olefin nonwoven fabric 14, and a pressure-sensitive adhesive layer for pasting 16 in order from the top and has a moisture permeability amount of 2000 g/(m²·24 hours) or more. In the medical pressure-sensitive adhesive sheet 1, the thickness of the urethane substrate 10 is a value within the range of from 1 to 10 μm, the thickness of the interlayer adhesive layer 12 is a value within the range of from 5 to 30 μm, the olefin nonwoven fabric 14 is constituted with a polypropylene-based thermoplastic elastomer and has a maximum point elongation percentage of a value of 200% or more in the longitudinal direction and the transverse direction, respectively, and the thickness of the pressure-sensitive adhesive layer for pasting 16 is a value within the range of from 5 to 45 μm.

Hereinafter, the medical pressure-sensitive adhesive sheet of the first embodiment will be described in detail by appropriately referring to the drawings.

1. Urethane Substrate (1) Kind

The kind of the urethane resin constituting the urethane substrate 10 illustrated in FIG. 1A or the like is not basically particularly limited as long as the urethane resin is a condensation reaction product of a polyisocyanate compound and an alcohol compound, and examples thereof may include a polyester urethane resin, a polyether urethane resin, a polycarbonate urethane resin, and an epoxy urethane resin.

More specifically, examples of the polyisocyanate compound constituting the urethane resin may include one kind or a combination of two or more kinds of tetramethylene diisocyanate, hexamethylene diisocyanate, trimethylhexamethylene diisocyanate, isophorone diisocyanate, 4,4'-methylenebis (cyclohexyl isocyanate), xylylene diisocyanate, tolylene diisocyanate, diphenylmethane diisocyanate, polyphenylmethane diisocyanate and the like.

In addition, examples of the alcohol compound constituting the urethane resin may include one kind or a combination of two or more kinds of a polyester polyol, a polyether polyol, a polycarbonate polyol, a polyacetal polyol, a polyacrylate polyol, a polyester amide polyol, a polythioether polyol and the like.

Furthermore, as a component constituting the urethane resin, a polyamine-based chain extender may be blended in a predetermined amount.

Examples of such a polyamine-based chain extender may include one kind or a combination of two or more kinds of ethylenediamine, 1,2-propanediamine, 1,6-hexamethylenediamine, piperazine, 2,5-dimethylpiperazine, isophoronediamine, 4,4'-dicyclohexylmethanediamine, 3,3'-dimethyl-4,4'-dicyclohexylmethanediamine, 1,4-cyclohexanediamine, diethylenetriamine, dipropylenetriamine, triethylenetetramine and the like.

(2) Elongation Percentage

In addition, the elongation percentage of the urethane substrate measured in conformity with JIS K 7127 is preferably a value of 150% or more.

The reason for this is because excellent fitting feel is obtained and predetermined moisture retaining property is easily obtained regardless of the sweat rate in the case of pasting the medical pressure-sensitive adhesive sheet on the skin or the like when the elongation percentage of the urethane substrate is a value of 150% or more.

However, there is a case in which the mechanical strength significantly decreases or the kind of the usable urethane resin is excessively limited when the elongation percentage of the urethane substrate is excessively large.

Consequently, the elongation percentage of the urethane substrate is more preferably a value within the range of from 200 to 2000% and even more preferably a value within the range of from 300 to 1000%.

Meanwhile, the usability of the medical pressure-sensitive adhesive sheet is improved and it can be easily and accurately pasted on a predetermined place in the case of using an ultrathin urethane substrate having an elongation percentage of 300% or more and a thickness of 10 μm or less, and also the medical pressure-sensitive adhesive sheet can be easily produced even in the case of using such a urethane substrate, and thus it is preferable that a reinforcing peeling member is layered in advance.

Figure 1B:
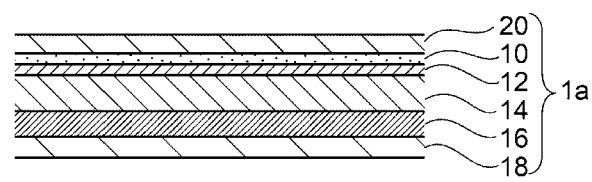

More specifically, as illustrated in FIG. 1B, it is preferable that a reinforcing peeling member 20 to function as a process sheet is layered on the surface of the urethane substrate 10 in advance.

(3) Thickness

In addition, the thickness of the urethane substrate is a value within the range of from 1 to 10 μm. The reason for this is because the mechanical strength decreases or it is difficult to adjust the value of the moisture permeability amount of the medical pressure-sensitive adhesive sheet when the thickness of the urethane substrate is a value of below 1 μm.

On the other hand, this is because there is a case in which not only the moisture permeability amount excessively decreases in the case of constituting the medical pressure-sensitive adhesive sheet and handling is difficult since it is thick but also it is easily recognizable from the outside and further it is easily peeled off from the skin when the thickness of the urethane substrate is a value of above 10 μm.

Consequently, the thickness of the urethane substrate is more preferably a value within the range of from 2 to 8 μm and even more preferably a value within the range of from 3 to 6 μm.

(4) Nonporosity

The urethane substrate is preferably nonporous.

In other words, this is because there is a case in which the elongation percentage of the urethane substrate changes or the moisture permeability excessively changes when the urethane substrate is porous.

Moreover, this is because there are problems that it is difficult to produce a urethane substrate having a uniform pore size and the manufacturing cost is high.

Meanwhile, in the case of the medical pressure-sensitive adhesive sheet of the invention, there is an advantage that a significantly great moisture permeability amount is obtained even when a nonporous urethane substrate is used since it is ultrathin.

(5) Coloring

Figure 1C:
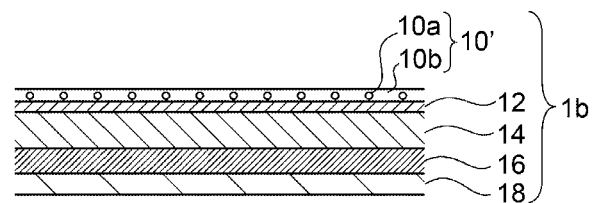

In addition, the urethane substrate may be colorless and transparent but is more preferably a colored urethane substrate 10' formed of a resin for urethane substrate 10b containing a colorant 10a as illustrated in FIG. 1C.

More specifically, the urethane substrate is preferably colored by containing at least one pigment or dye of a skin color, a black color, a green color, a red color, a brown color, a blue color, a purple color, a yellow color, a vermilion color or the like as the colorant in consideration of wearing stockings, socks or the like in the state of being pasted with a medical pressure-sensitive adhesive sheet (adhesive plasters or the like).

The reason for this is because the medical pressure-sensitive adhesive sheet (adhesive plasters or the like) can be far less recognizable from the outside via stockings, socks or the like at the time of using the medical pressure-sensitive adhesive sheet by coloring the urethane substrate in this way.

In addition, upon coloring the urethane substrate, the blending amount of the colorant such as a pigment or a dye is preferably a value within the range of from 0.01 to 10 parts by weight with respect to 100 parts by weight of the resin for urethane substrate.

The reason for this is because favorable colorability can be obtained without impairing the mechanical properties including elongation percentage of the urethane substrate according to such a constitution.

(6) Water Repellent Treated Layer

In addition, it is preferable to provide a water repellent treated layer (including a sizing layer) on the surface of the urethane substrate although not illustrated in the drawing.

The reason for this is because it is possible to effectively prevent the position shift or damage of the stockings, socks, or the like since the interference (friction) between the surface of the urethane substrate and these is reduced even in the case of wearing these in the state of being pasted with a medical pressure-sensitive adhesive sheet (adhesive plasters or the like) according to such a constitution.

Moreover, this is because it is possible to adjust the amount of water vapor and thus to effectively prevent peeling of the medical pressure-sensitive adhesive sheet by providing the water repellent treated layer.

Furthermore, this is because it is preferable in terms of hygienic environment since the ingress of a liquid substance from the outside can be easily prevented by providing the water repellent treated layer.

Meanwhile, such a water repellent treated layer is preferably constituted by a fluorocarbon resin or a silicone resin, for example.

(7) Moisture Permeability Amount

In addition, the moisture permeability amount of the urethane substrate measured in conformity with JIS Z 0208 is preferably a value within the range of from 3,000 to 10,000 g/(m²·24 hours) although it also depends on the thickness (1 to 10 μm) of the urethane substrate.

The reason for this is because the moisture permeability amount of medical pressure-sensitive adhesive sheet itself is adjusted to a value within a predetermined range by controlling the moisture permeability amount of the urethane substrate within this range, and thus it is possible to control the moisture retaining property or to effectively prevent peeling of the medical pressure-sensitive adhesive sheet.

Moreover, this is because it is preferable in terms of hygienic environment since the ingress of a liquid substance from the outside can be easily prevented by controlling the moisture permeability amount of the urethane substrate in this way.

Consequently, the moisture permeability amount of the urethane substrate is more preferably a value within the range of from 4,000 to 8,000 g/(m²·24 hours) and even more preferably a value within the range of from 5,000 to 7,000 g/(m²·24 hours).

(8) Identification Mark and Decorative Layer

Figure 1D:
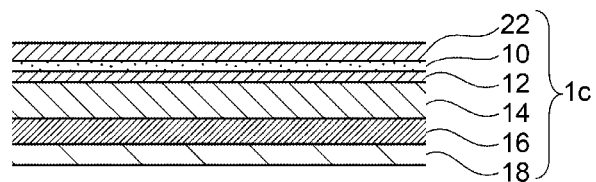

In addition, it is preferable that an identification mark or a decorative layer is provided on the surface or the back surface of the urethane substrate 10 as a resin layer 22 as illustrated in FIG. 1D.

The reason for this is because it is possible to easily select the desired medical pressure-sensitive adhesive sheet from a plurality of medical pressure-sensitive adhesive sheets different in sizes or shapes by providing a numeral mark, a Chinese character mark, a pictogram mark, a Braille mark, or the like and thus it is possible to significantly improve the usability of a medical pressure-sensitive adhesive sheet.

Moreover, this is because not only the usability of the medical pressure-sensitive adhesive sheet is improved but also the value on the fissionability can be improved by providing a decorative layer that represents a numeral pattern, a Chinese character pattern, a pictogram pattern, a photograph pattern, or the like as such a decorative layer. For example, it is also possible to enhance the recognizability at night by providing a decorative layer containing a fluorescent agent.

2. Interlayer Adhesive Layer (1) Kind

The kind of the interlayer adhesive layer is not particularly limited and is preferably a urethane-based adhesive, for example.

In other words, this is because it is possible to exhibit favorable adhesiveness even with respect to the ultrathin urethane substrate described above and to effectively prevent peeling between the urethane substrate and the olefin nonwoven fabric when the interlayer adhesive layer is a urethane-based adhesive.

Moreover, this is because it is possible to prevent an excessive decrease in the moisture permeability amount in a case in which a medical pressure-sensitive adhesive sheet is constituted as well as the predetermined flexibility or elongation is exhibited when the interlayer adhesive layer is a urethane-based adhesive.

Hence, it is preferable to use basically a thermosetting resin (crosslinkable resin) formed by a combination of a polyol compound and an isocyanate curing agent as the urethane-based adhesive.

More specifically, examples of the polyol compound may include one kind or a combination of two or more kinds of a polyester polyol, an acrylic polyol, a fluorine-containing polyol, a lactone polyol, a polyether polyol, a polycarbonate polyol, an aromatic polyol and the like.

In addition, it is possible to use an aromatic polyisocyanate compound and an aliphatic polyisocyanate compound or either of them as the isocyanate curing agent.

Examples of the aromatic polyisocyanate compound may include at least one kind of p-phenylene diisocyanate, m-phenylene diisocyanate, p-xylene diisocyanate, m-xylene diisocyanate, 2,4-tolylene diisocyanate, 2,6-tolylene diisocyanate, 4,4'-diphenylmethane diisocyanate, 3,3'-dimethyldiphenyl-4,4'-diisocyanate, 3,3'-diethyldiphenyl-4,4'-diisocyanate, 1,3-bis(α,α-dimethyl isocyanate methyl)benzene, tetramethylxylylene diisocyanate, and diphenylene ether-4,4'-diisocyanate, naphthalene diisocyanate and the like.

Examples of the aliphatic polyisocyanate compound may include at least one kind of hexamethylene diisocyanate, lysine diisocyanate, trimethylhexamethylene diisocyanate, isophorone diisocyanate, 4,4'-dicyclohexylmethane diisocyanate, hydrogenatedxylene diisocyanate, norbornene diisocyanate and the like.

(2) Thickness

In addition, the thickness of the interlayer adhesive layer is a value within the range of from 5 to 30 μm.

The reason for this is because the moisture permeability amount of medical pressure-sensitive adhesive sheet or a composite sheet itself is adjusted to a value within a predetermined range by controlling the thickness of the interlayer adhesive layer within this range, and thus it is possible to control the moisture retaining property and also to effectively prevent peeling between the urethane substrate and the olefin nonwoven fabric.

More specifically, this is because there is a case in which the mechanical strength or the adhesive strength decreases and thus it is difficult to effectively prevent peeling between the urethane substrate and the olefin nonwoven fabric when the thickness of the interlayer adhesive layer is a value of below 5 μm.

On the other hand, this is because there is a case in which the flexibility or maximum point elongation percentage of the urethane/olefin composite substrate excessively decreases in a case in which the urethane/olefin composite substrate formed by layering the urethane substrate and the olefin nonwoven fabric via the interlayer adhesive layer is constituted or further the moisture permeability amount of the medical pressure-sensitive adhesive sheet excessively decreases when the thickness of the interlayer adhesive layer is a value of above 30 μm.

Consequently, the thickness of the interlayer adhesive layer is more preferably a value within the range of from 6 to 20 μm and even more preferably a value within the range of from 8 to 15 μm.

(3) Adhesive Force

In addition, it is preferable that the peel strength between the urethane substrate and the olefin nonwoven fabric layered via the interlayer adhesive layer is a value within the range of from 2 to 20 N/25 mm.

The reason for this is because by limiting the value of the peel strength within this range it is possible to obtain favorable mechanical strength or adhesive strength while maintaining favorable maximum point elongation percentage or flexibility in a case in which the urethane/olefin composite substrate and furthermore the medical pressure-sensitive adhesive sheet are constituted.

Consequently, the peel strength between the urethane substrate and the olefin nonwoven fabric is more preferably a value within the range of from 3 to 15 N/25 mm and even more preferably a value within the range of from 5 to 12 N/25 mm.

Meanwhile, the peel strength between the urethane substrate and the olefin nonwoven fabric can be measured in conformity with JIS L 1086 as the T-type peel strength.

3. Olefin Nonwoven Fabric (1) Kind

In addition, the olefin nonwoven fabric is constituted with a polypropylene-based thermoplastic elastomer (including a polypropylene • polyethylene-based thermoplastic elastomer or a polyethylene-based thermoplastic elastomer).

In other words, the predetermined mechanical strength is obtained and also favorable elongation or flexibility is obtained when the olefin nonwoven fabric is composed of a polypropylene-based thermoplastic elastomer.

Here, the content of the polypropylene-based thermoplastic elastomer constituting the olefin nonwoven fabric is preferably a value of above 95% by weight with respect to the total amount of the raw material of the olefin nonwoven fabric.

In other words, the olefin nonwoven fabric can also be constituted with a mixture of a polypropylene-based thermoplastic elastomer and a polypropylene resin or the like, but even in that case, the content of the polypropylene-based thermoplastic elastomer is preferably a value of above 95% by weight with respect to the total amount (100% by weight) of the raw material.

The reason for this is because there is a case in which the maximum elongation percentage or resiliency of the olefin nonwoven fabric significantly decreases or further it is difficult to adjust the peel strength between the urethane substrate and the olefin nonwoven fabric to a value within a predetermined range in a case in which the urethane/olefin composite substrate is constituted with the urethane substrate and the olefin nonwoven fabric via the interlayer adhesive layer described above when the content of the polypropylene-based thermoplastic elastomer is a value of 95% by weight or less.

Consequently, the content of the polypropylene-based thermoplastic elastomer is more preferably a value within the range of from 96 to 99% by weight and even more preferably a value within the range of from 97 to 98% by weight with respect to the total amount (100% by weight) of the raw material of the olefin nonwoven fabric in a case in which the olefin nonwoven fabric is constituted with a mixture of a polypropylene-based thermoplastic elastomer and a polypropylene resin or the like.

In addition, the MFR (melt flow rate) of the polypropylene-based thermoplastic elastomer contained in the olefin nonwoven fabric is preferably a value within the range of from 1 to 48 g/10 minutes (temperature: 230° C.)

In other words, this is because a balance between the favorable production efficiency of the olefin nonwoven fabric and the mechanical strength or the maximum elongation percentage is favorable by adjusting the MFR of the polypropylene-based thermoplastic elastomer to the value within the predetermined range.

More specifically, this is because there is a case in which the heating temperature excessively increases or the production efficiency excessively deteriorates in the case of producing the olefin nonwoven fabric by the melt blow method when the MFR of the polypropylene-based thermoplastic elastomer is a value of below 1 g/10 minutes.

On the other hand, this is because there is a case in which the mechanical strength or the maximum elongation percentage of the olefin nonwoven fabric obtained is an excessively low value when the MFR of the polypropylene-based thermoplastic elastomer is a value of 48 g/10 minutes or more.

Consequently, the MFR of the polypropylene-based thermoplastic elastomer contained in the olefin nonwoven fabric is more preferably a value within the range of from 5 to 45 g/10 minutes (temperature: 230° C.) and even more preferably a value within the range of from 8 to 40 g/10 minutes (temperature: 230° C.)

Meanwhile, the MFR of the polypropylene-based thermoplastic elastomer can be measured in conformity with JIS K 7210.

(2) Maximum Point Elongation Percentage

The maximum point elongation percentage of the olefin nonwoven fabric is a value of 200% or more in a longitudinal direction and a transverse direction, respectively.

The reason for this is because favorable elongation percentage is obtained in each of the longitudinal direction (flow direction) and a transverse direction (90° direction with respect to the flow direction) at the time of the production in the case of constituting the urethane/olefin composite substrate and furthermore the medical pressure-sensitive adhesive sheet when the maximum point elongation percentage in each of the longitudinal and transverse directions is equal to or more than a predetermined value.

On the contrary, this is because the elongation percentage is excessively limited and thus the usability thereof significantly deteriorates in the case of constituting a medical pressure-sensitive adhesive sheet when the maximum point elongation percentage in one direction is a value of below 200% although the maximum point elongation percentage in the other direction is a value of equal to or more than 200% with regard to the maximum point elongation percentage of the olefin nonwoven fabric in the longitudinal and transverse directions.

However, there is a case in which resiliency or the like deteriorates when the maximum point elongation percentage is excessively large in each of the longitudinal and transverse directions.

Consequently, the maximum point elongation percentage of the olefin nonwoven fabric is more preferably a value of within the range of from 300 to 800% and even more preferably a value of within the range of from 350 to 600% in the longitudinal direction and the transverse direction, respectively.

Meanwhile, the maximum point elongation percentage of the olefin nonwoven fabric in the longitudinal direction and the transverse direction can be measured using, for example, the tensile testing apparatus Strograph VE5D (manufactured by Toyo Seiki Co., Ltd.) in conformity with JIS L 1913.

Figure 2A:
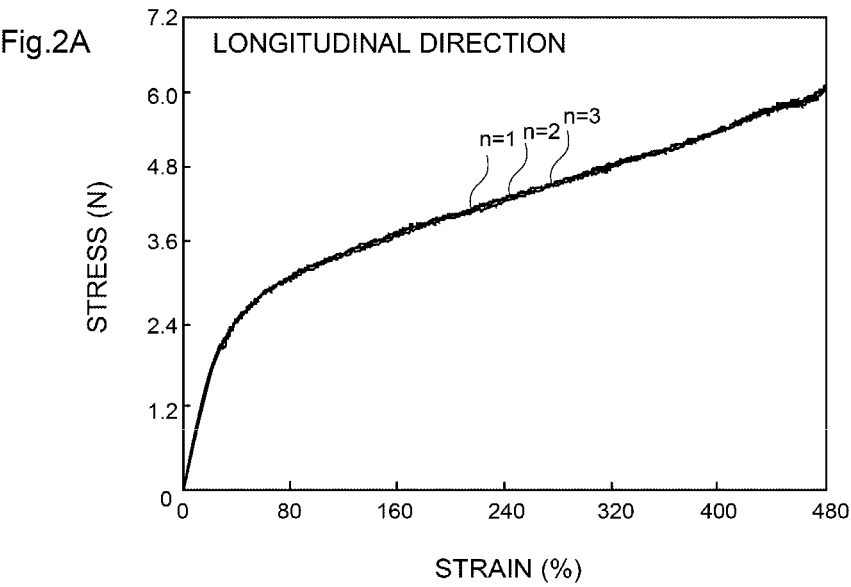
FIGS. 2A and 2B are stress-strain curves of an olefin nonwoven fabric consisting of only a predetermined thermoplastic elastomer (corresponding to Example 1, longitudinal direction and transverse direction) by a melt blow method.
Figure 2B:
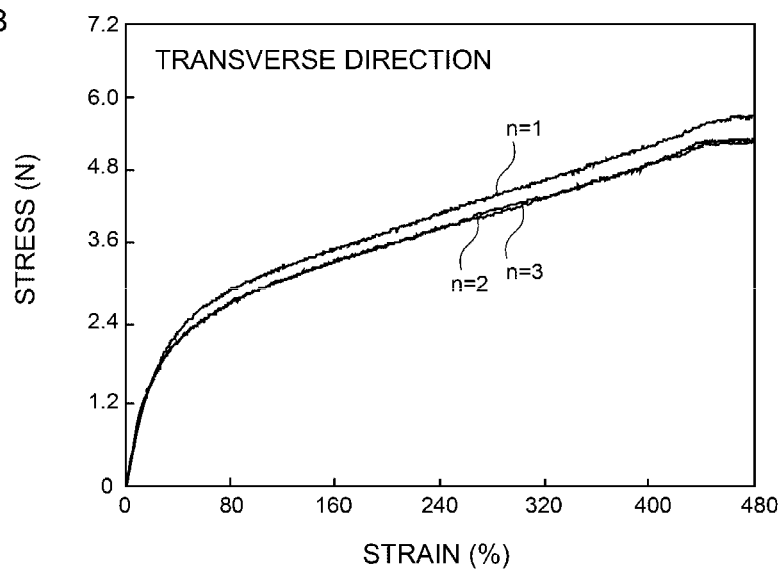

Here, the characteristic curves (n1 to n3) in FIGS. 2A and 2B represent the stress-strain curve (longitudinal direction and transverse direction) of the olefin nonwoven fabric (corresponding to Example 1) produced by the melt blow method using a predetermined thermoplastic elastomer (100% by weight) as the raw material.

In addition, there are three characteristic curves (n1 to n3) since the variation of the same olefin nonwoven fabric (three samples) has been investigated.

In other words, as illustrated in FIGS. 2A and 2B, there has been observed a tendency that the stress steeply increases to about from 3 to 4 N until the strain increases to about 80%, but the stress gradually increases to be from 5 to 6 N when the strain increases from above 80% to 480% in each of the directions.

Moreover, it has been verified that at least the olefin nonwoven fabric does not rupture even when the strain is a value of above 480% in each of the longitudinal and transverse directions.

Consequently, it has been verified that the maximum point elongation percentage of the olefin nonwoven fabric is a value of 480% or more in each of the longitudinal and transverse directions while the stress generated is relatively low and thus it can be said that excellent extensibility is exhibited in the case of constituting not only an olefin nonwoven fabric urethane/olefin composite substrate but also a medical pressure-sensitive adhesive sheet when the olefin nonwoven fabric is used.

Incidentally, it has also been verified that there is little variation between the samples in the stress-strain curves illustrated in FIGS. 2A and 2B.

Figure 3A:
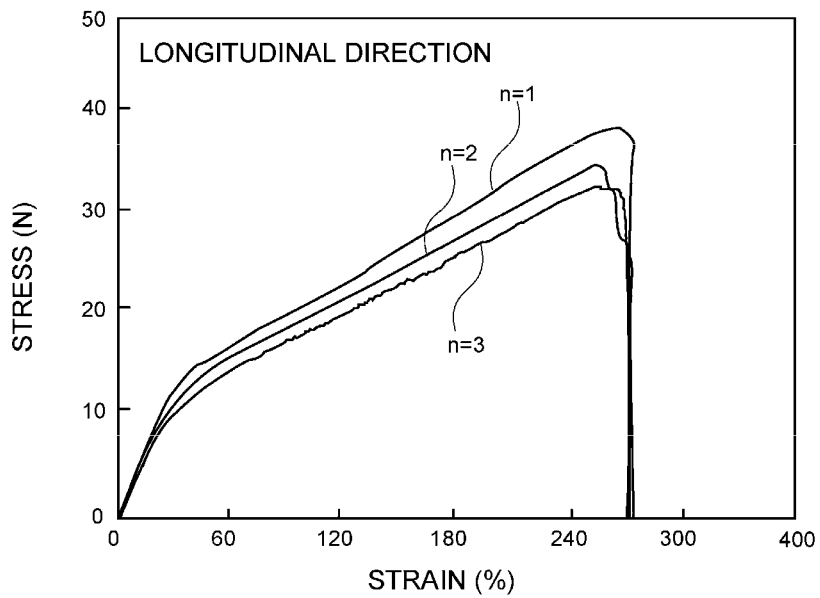
FIGS. 3A and 3B are stress-strain curves of an olefin nonwoven fabric consisting of a mixture of predetermined thermoplastic elastomer/polypropylene resin (corresponding to Example 5, longitudinal direction and transverse direction) by a spunbond method.
Figure 3B:
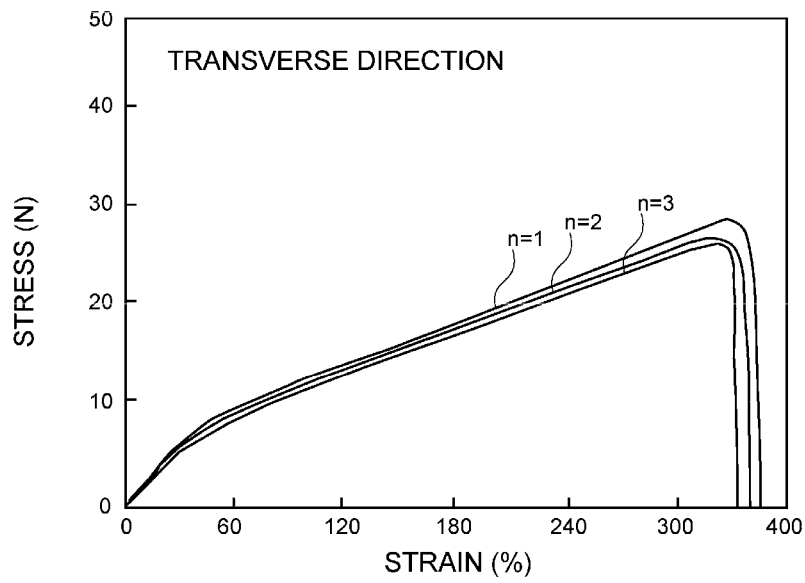

In addition, the characteristic curves (n1 to n3) in FIGS. 3A and 3B represent the stress-strain curve (longitudinal direction and transverse direction) of a predetermined olefin nonwoven fabric (corresponding to Example 5) produced by the spunbond method using a polypropylene-based thermoplastic elastomer/polypropylene mixture as the raw material.

In other words, as illustrated in FIGS. 3A and 3B, there has been observed a tendency that the stress steeply increases to about from 10 to 15 N until the strain increases to about 60%, but the stress gradually increases to be approximately from 20 to 25 N when the strain increases from above 60% to 240% in each of the directions.

Moreover, it has been verified that the olefin nonwoven fabric ruptures when the strain is a value of above 250% and 300% in the longitudinal direction and the transverse direction, respectively.

Hence, it has been verified that the extensibility in the longitudinal and transverse directions is not so high although the maximum point elongation percentage of the olefin nonwoven fabric is a value of 200% or more in each of the longitudinal and transverse directions.

Consequently, it can be said that there is a case in which the extensibility is insufficient in the case of constituting not only a urethane/olefin composite substrate but also a medical pressure-sensitive adhesive sheet.

Incidentally, it has also been verified that there is slightly large variation between the samples in the stress-strain curves illustrated in FIGS. 3A and 3B.

Accordingly, it can be said that the olefin nonwoven fabric produced by the melt blow method using only a thermoplastic elastomer (100% by weight) as the raw material exhibits the most favorable extensibility although the stress generated is not a so large value from the comparison of the stress-strain curves (longitudinal direction and transverse direction) illustrated in FIGS. 2A and 2B and FIGS. 3A and 3B.

On the other hand, it can be said that the olefin nonwoven fabric produced by the spunbond method using a polypropylene-based thermoplastic elastomer/polypropylene mixture as the raw material exhibits relatively deteriorated elongation properties although the stress generated is relatively great.

Accordingly, in the invention, it is comprehended that the olefin nonwoven fabric produced by the melt blow method using a thermoplastic elastomer as the main raw material exhibits the most favorable usability since the elongation properties thereof in the longitudinal and transverse directions are favorable and the stress generated is relatively small.

(3) 100% Modulus

In addition, the 100% modulus (taken the value for the longitudinal direction as the representative value) of the olefin nonwoven fabric is preferably a value within the range of from 2 to 30 N/50 mm.

The reason for this is because the deterioration in the elasticity of the olefin nonwoven fabric is suppressed and thus it is possible to maintain favorable elasticity or flexibility or mechanical strength of the entire medical pressure-sensitive adhesive sheet by controlling the 100% modulus within this range.

More specifically, this is because there is a case in which the olefin nonwoven fabric is extended with a slight stress and thus the handleability thereof excessively deteriorates when the 100% modulus of the olefin nonwoven fabric is a value of below 2 N/50 mm.

On the other hand, this is because there is a case in which the followability deteriorates or the texture (sense of touch) is excessively hard when the 100% modulus of the olefin nonwoven fabric is a value of above 30 N/50 mm.

Consequently, the 100% modulus of the olefin nonwoven fabric is more preferably a value within the range of from 3 to 15 N/50 mm and even more preferably a value within the range of from 5 to 10 N/50 mm.

(4) Mass Per Unit Area

In addition, the mass per unit area of the olefin nonwoven fabric is preferably a value within the range of from 10 to 100 $g/m^2$.

The reason for this is because it is possible to effectively prevent peeling between the urethane substrate and the olefin nonwoven fabric as well as the moisture permeability amount or cushioning properties is adjusted to a value within a predetermined range in the case of constituting a medical pressure-sensitive adhesive sheet so that the moisture retaining property or usability can be controlled by controlling the mass per unit area of the olefin nonwoven fabric within this range.

More specifically, this is because there is a case in which the handleability or cushioning properties excessively deteriorate in the case of constituting a medical pressure-sensitive adhesive sheet when the mass per unit area of the olefin nonwoven fabric is a value of below 10 $g/m^2$.

On the other hand, this is because there is a case in which peeling between the urethane substrate and the olefin nonwoven fabric easily occurs or the moisture permeability amount decreases in the case of constituting a medical pressure-sensitive adhesive sheet when the mass per unit area of the olefin nonwoven fabric is a value of above 100 $g/m^2$.

Consequently, the mass per unit area of the olefin nonwoven fabric is more preferably a value within the range of from 20 to 80 $g/m^2$ and even more preferably a value within the range of from 30 to 60 $g/m^2$.

4. Urethane/Olefin Composite Substrate (1) Thickness

The thickness of the urethane/olefin composite substrate is preferably a value within the range of from 15 to 80 µm.

The reason for this is because it is possible to effectively prevent peeling between the urethane substrate and the olefin nonwoven fabric as well as the moisture permeability amount or cushioning properties is adjusted to a value within a predetermined range in the case of constituting a medical pressure-sensitive adhesive sheet so that the moisture retaining property or usability can be controlled by controlling the thickness of the urethane/olefin composite substrate within this range.

More specifically, this is because there is a case in which the handleability or cushioning properties excessively deteriorate in the case of constituting a medical pressure-sensitive adhesive sheet when the thickness of the urethane/olefin composite substrate is a value of below 15 μm.

On the other hand, this is because there is a case in which peeling between the urethane substrate and the olefin nonwoven fabric easily occurs or the moisture permeability amount decreases in the case of constituting a medical pressure-sensitive adhesive sheet when the thickness of the urethane/olefin composite substrate is a value of above 80 μm.

Consequently, the thickness of the urethane/olefin composite substrate is more preferably a value within the range of from 20 to 60 μm and even more preferably a value within the range of from 30 to 50 μm.

(2) Stress-Strain Curve

Figure 4A:
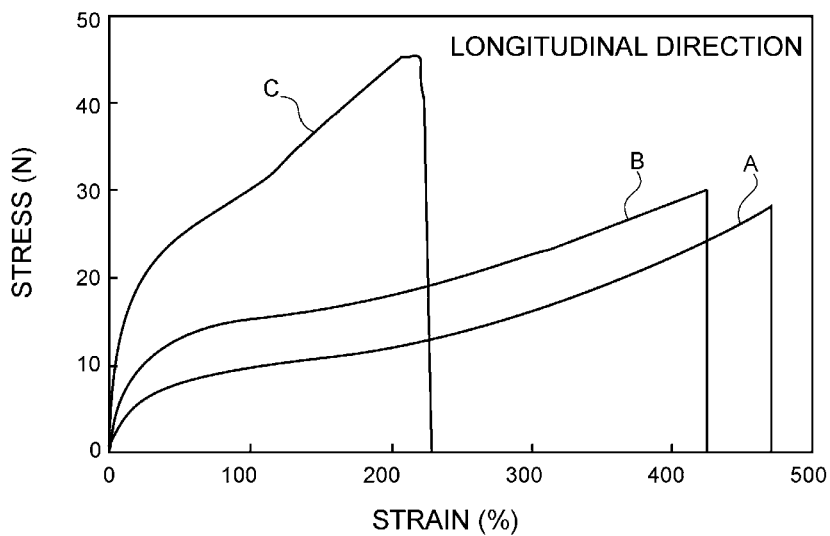
FIGS. 4A and 4B are stress-strain curves of a urethane/olefin composite substrate consisting of various kinds of urethane substrate/interlayer adhesive layer/olefin nonwoven fabric (longitudinal direction and transverse direction)
Figure 4B:
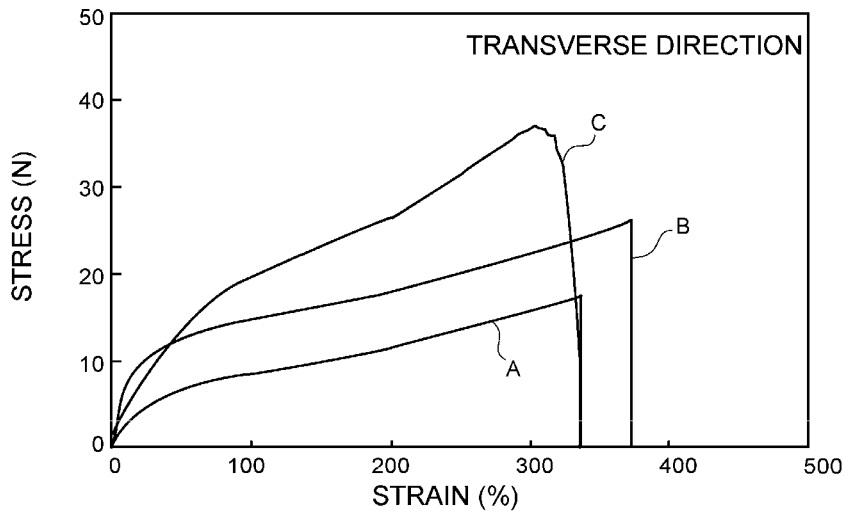

Next, the line A in FIGS. 4A and 4B represents the stress-strain curve (longitudinal direction and transverse direction) of the urethane/olefin composite substrate (corresponding to Example 1) formed using the olefin nonwoven fabric produced by the melt blow method using only a predetermined polypropylene-based thermoplastic elastomer (100% by weight) as the raw material.

In addition, the line B in the same drawings represents the stress-strain curve (longitudinal direction and transverse direction) of the urethane/olefin composite substrate (corresponding to Example 4) formed using the olefin nonwoven fabric produced by the melt blow method using a polypropylene-based thermoplastic elastomer/polypropylene mixture (weight ratio=75/25) as the raw material.

Furthermore, the line C in the same drawings represents the stress-strain curve (longitudinal direction and transverse direction) of the urethane/olefin composite substrate (corresponding to Example 5) formed using the olefin nonwoven fabric produced by the spunbond method using a polypropylene-based thermoplastic elastomer/polypropylene mixture (weight ratio=75/25) as the raw material.

First, it can be said that the value of the maximum point elongation percentage is considerably great to be 473% and 337% in the longitudinal direction and the transverse direction, respectively, and the difference between them is relatively great to be 136% in the case of the stress-strain curve represented by line A.

Moreover, it can be said that the value of the maximum point load is reasonably great to be 27 N and 17 N in the longitudinal direction and the transverse direction, respectively, and the difference between them is relatively great to be 10 N in the case of the stress-strain curve represented by line A, and thus reasonable mechanical strength is exhibited in both the longitudinal direction and the transverse direction.

In addition, it can be said that the value of the maximum point elongation percentage is considerably great to be 416% and 365% in the longitudinal direction and the transverse direction, respectively, and the difference between them is relatively moderate to be 51% in the case of the stress-strain curve represented by line B.

Moreover, it can be said that the value of the maximum point load is reasonably great to be 30 N and 25 N in the longitudinal direction and the transverse direction, respectively, and the difference between them is relatively small to be 5 N in the case of the stress-strain curve represented by line B, and thus reasonable mechanical strength is exhibited in both the longitudinal direction and the transverse direction.

Furthermore, it can be said that the value of the maximum point elongation percentage is relatively small to be 219% and 304% in the longitudinal direction and the transverse direction, respectively, and the difference between them is relatively moderate to be 85% in the case of the stress-strain curve represented by line C.

Moreover, it can be said that the value of the maximum point load is considerably great to be 44 N and 35 N in the longitudinal direction and the transverse direction, respectively, and the difference between them is relatively moderate to be 9 N in the case of the stress-strain curve represented by line C, and thus reasonable mechanical strength is exhibited in both the longitudinal direction and the transverse direction.

In other words, from the comparison of these lines A to C, it can be said that the urethane/olefin composite substrate formed using the olefin nonwoven fabric produced by the melt blow method using only a polypropylene-based thermoplastic elastomer (100% by weight) as the raw material exhibits relatively greatly anisotropic elongation properties and mechanical strength.

In addition, it can be said that the urethane/olefin composite substrate formed using the olefin nonwoven fabric produced by the melt blow method using a polypropylene-based thermoplastic elastomer/polypropylene mixture as the raw material exhibits relatively greatly isotropic elongation properties and mechanical strength.

Furthermore, it can be said that the olefin nonwoven fabric produced using a polypropylene-based thermoplastic elastomer/polypropylene mixture as the raw material by the spunbond method exhibits reasonably anisotropic elongation properties and mechanical strength although the value of the rupture stress itself is relatively great.

Accordingly, it is comprehended that in the medical pressure-sensitive adhesive sheet of the invention that regards extensibility as important, the urethane/olefin composite substrate formed using the olefin nonwoven fabric produced by the melt blow method using a polypropylene-based thermoplastic elastomer as the main raw material is suitable since it exhibits considerable mechanical strength as well as excellent elongation properties in the longitudinal and transverse directions as illustrated in lines A and B.

(3) 100% Modulus

In addition, the 100% modulus of the urethane/olefin composite substrate (taken the value for the longitudinal direction as the representative value) is preferably a value within the range of from 3 to 40 N/50 mm.

The reason for this is because it is possible to suppress the deterioration in the elasticity of the urethane/olefin composite substrate and thus to maintain favorable elasticity or flexibility or mechanical strength of the entire medical pressure-sensitive adhesive sheet by controlling the 100% modulus within this range.

More specifically, this is because there is a case in which the urethane/olefin composite substrate is extended with a slight stress and thus the handleability thereof excessively deteriorates when the 100% modulus of the urethane/olefin composite substrate is a value of below 3 N/50 mm.

On the other hand, this is because there is a case in which the followability deteriorates or the texture (sense of touch) of the urethane/olefin composite substrate is excessively hard when the 100% modulus of the urethane/olefin composite substrate is a value of above 40 N/50 mm.

Consequently, the 100% modulus of the urethane/olefin composite substrate is more preferably a value within the range of from 5 to 30 N/50 mm and even more preferably a value within the range of from 10 to 20 N/50 mm.

5. Pressure-Sensitive Adhesive Layer for Pasting (1) Kind

The kind of the adhesive constituting the pressure-sensitive adhesive layer for pasting 16 illustrated in FIG. 1C is not particularly limited, but the pressure-sensitive adhesive layer for pasting is preferably constituted with at least one kind of an acrylic pressure-sensitive adhesive or an olefin-based pressure-sensitive adhesive which contains a crosslinking agent, a rubber-based pressure-sensitive adhesive, or a silicone pressure-sensitive adhesive.

This is because, for example, an acrylic pressure-sensitive adhesive containing a crosslinking agent also exhibits creep resistance, water resistance, and further chemical resistance while it is relatively inexpensive and able to exhibit proper stickiness with respect to the skin of the human body or the olefin nonwoven fabric.

In addition, this is because an olefin-based adhesive containing a crosslinking agent also exhibits water resistance or chemical resistance while it is relatively inexpensive and able to exhibit proper stickiness with respect the olefin nonwoven fabric.

In addition, a rubber-based adhesive can be formed into a solventless type hot melt pressure-sensitive adhesive by containing a predetermined amount of tackifier and thus it is not only environmentally friendly but also economical since a large amount of solvent is not used therein, and further it can exhibit relatively high adhesive force with respect to the skin of the human body or the olefin nonwoven fabric.

Furthermore, it is possible to obtain an advantage that favorable affinity is exhibited for the skin of the human body and peeling hardly occurs when it is adhered by using an organopolysiloxane-based pressure-sensitive adhesive.

(2) Crosslinking Agent or the Like

In addition, it is preferable that, for example, an isocyanate compound is usually blended in the range of from 0.1 to 10% by weight with respect to the total amount of the pressure-sensitive adhesive in order to partly crosslink an acrylic pressure-sensitive adhesive or an olefin-based pressure-sensitive adhesive and to improve stickiness at a high temperature.

In other words, it is possible to introduce a hydroxyl group into the molecule of the acrylic pressure-sensitive adhesive or the olefin-based pressure-sensitive adhesive using a hydroxyl group-containing vinyl monomer at the time of the polymerization. Hence, it is possible to partly introduce a crosslinked structure into the acrylic pressure-sensitive adhesive or the olefin-based pressure-sensitive adhesive by allowing the hydroxyl group to react with an isocyanate compound.

In addition, it is preferable to add a curing catalyst such as an organic peroxide such as benzoyl peroxide or dicumyl peroxide or platinum catalyst in the range of from 1.5 to 3% by weight with respect to the solid content of the organopolysiloxane-based pressure-sensitive adhesive in the case of the organopolysiloxane-based pressure-sensitive adhesive.

Meanwhile, it is preferable to perform a heat treatment at a temperature for the aging treatment (at 50° C. for 7 days) or the heat treatment (at 120° C. or higher for 1 to 30 minutes) after adding an isocyanate compound or an organic peroxide or platinum catalyst so that the effect of adding the crosslinking agent or the like is effectively exerted.

(3) Additive

In addition, a formulation (drug) can be added into the pressure-sensitive adhesive composition as one kind of additive so that the predetermined drug efficacy can be exerted.

The kind of such a formulation is not particularly limited, and examples thereof may include one kind or a combination of two or more kinds of anti-inflammatory drug, antiphlogistic analgetic, coronary vasodilators, asthma drug, anti-hypertensive agent, antihistamines, tranquilizers, antibiotics, anesthetics, vitamins, and the like.

In addition, it is preferable that the addition amount of the formulation is, for example, a value within the range of from 0.1 to 30% by mass with respect to the total amount of the pressure-sensitive adhesive composition although it depends on the kind of the formulation or the application of the pressure-sensitive adhesive composition.

In addition, various kinds of additives are preferably added into the pressure-sensitive adhesive composition. Examples thereof may include one kind or a combination of two or more kinds of an antioxidant, a viscosity modifier, an ultraviolet absorber, an opacifying agent, a plasticizer, a wax, a colorant, an inorganic filler, an organic filler, an extender, a coupling agent and the like.

(4) Adhesive Force

In addition, the adhesive force (peel force in 180° direction measured in conformity with JIS Z 0237, adherend: stainless steel plate, peel rate: 300 ram/min) of the medical pressure-sensitive adhesive sheet is preferably a value within the range of from 2 to 20 N/25 mm.

The reason for this is because there is a case in which the medical pressure-sensitive adhesive sheet is easily peeled off from the skin or the like and thus is poor in function as a medical pressure-sensitive adhesive sheet when the adhesive force is a value of below 2 N/25 mm.

On the other hand, this is because there is a case in which it is difficult to remove the pressure-sensitive adhesive from the skin or skin irritation is excessively high and thus unpleasantness is caused at the time of use when the adhesive strength is a value of above 20 N/25 mm.

Consequently, the adhesive force of the medical pressure-sensitive adhesive sheet as a single item is more preferably a value within the range of from 4 to 15 N/25 mm and even more preferably a value within the range of from 6 to 13 N/25 mm.

Meanwhile, the thickness of the pressure-sensitive adhesive layer for pasting is preferably a value within the range of from 5 to 45 μm, more preferably a value within the range of from 8 to 30 μm, and even more preferably a value within the range of from 10 to 20 μm in order to control the value of the adhesive force within this range.

6. Release Sheet

In addition, a release sheet 18 is preferably layered on the surface of the pressure-sensitive adhesive layer for pasting 16 as illustrated in FIG. 1A or the like.

This is because the handleability of the medical pressure-sensitive adhesive sheet is improved even if a thin urethane substrate is included therein as well as the protection of the pressure-sensitive adhesive layer for pasting is achieved by layering such a release sheet.

Here, the aspect of the release sheet is not particularly limited, but more specifically, the release sheet is divided into three parts and is constituted with a left end release sheet, a central release sheet, and a right end release sheet, and also part of each of the left end release sheet and the right end release sheet is folded so as to provide a hand hold in the case of a medical pressure-sensitive adhesive sheet such as an adhesive plaster.

The reason for this is because handling of the medical pressure-sensitive adhesive sheet can be further facilitated although it has a simple structure including a thin urethane substrate according to such a constitution including a release sheet.

7. Moisture Permeability Amount

In addition, the moisture permeability amount of the medical pressure-sensitive adhesive sheet measured in conformity with JIS Z 0208 is a value of 2000 g/(m$^2$·24 hours) or more.

The reason for this is because it is possible to effectively prevent peeling of the medical pressure-sensitive adhesive sheet since not only proper moisture retaining property is obtained but also favorable cohesiveness is obtained regardless of the amount of the sweat rate at the pasting location by controlling the moisture permeability amount of the medical pressure-sensitive adhesive sheet within this range.

More specifically, this is because water vapor due to sweating or the like is excessively accumulated between the pasting location and the medical pressure-sensitive adhesive sheet and thus the medical pressure-sensitive adhesive sheet is easily peeled off when the moisture permeability amount of the medical pressure-sensitive adhesive sheet is a value of below 2000 g/(m²·24 hours).

On the other hand, there is a case in which the kind of the usable materials is excessively limited when the moisture permeability amount of the medical pressure-sensitive adhesive sheet is excessively great.

Consequently, the moisture permeability amount of the medical pressure-sensitive adhesive sheet is more preferably a value within the range of from 2500 to 8000 g/(m²·24 hours) and even more preferably a value within the range of from 3000 to 6000 g/(m²·24 hours).

8. Water Bearing Pressure

In addition, the water bearing pressure of the medical pressure-sensitive adhesive sheet measured in conformity with method B (high water pressure method) of JIS L 1092 is preferably 500 mm H₂O or more.

The reason for this is because there is a case in which use in the application requiring water resistance is limited and thus the application of the medical pressure-sensitive adhesive sheet is excessively limited when the water bearing pressure is a value of below 500 mm H₂O.

However, there is a case in which the kind or the like of the urethane substrate, the olefin nonwoven fabric or the like usable in the medical pressure-sensitive adhesive sheet is excessively limited in turn when the value of the water bearing pressure is excessively great.

Consequently, the water bearing pressure of the medical pressure-sensitive adhesive sheet is preferably a value within the range of 800 to 2000 mm H₂O and more preferably a value within the range of 1000 to 1500 mm H₂O.

[Second Embodiment]

As illustrated in FIGS. 5A to 5E, a second embodiment is a method for producing a medical pressure-sensitive adhesive sheet 1 including a urethane substrate 10 having a thickness of from 1 to 10 μm, an interlayer adhesive layer 12 having a thickness of from 5 to 30 μm, an olefin nonwoven fabric 14 constituted with a polypropylene-based thermoplastic elastomer and having a maximum point elongation percentage of a value of 300% or more in a longitudinal direction and a transverse direction, respectively, and a pressure-sensitive adhesive layer for pasting 16 having a thickness of from 5 to 45 μm, in order from the bottom, and having a moisture permeability amount of 2000 g/(m²·24 hours) or more, which includes the following processes (1) and (2).

(1) a process of layering the urethane substrate 10 and the olefin nonwoven fabric 14 via the interlayer adhesive layer 12 to form a urethane/olefin composite substrate 15 and (2) a process of forming the pressure-sensitive adhesive layer for pasting 16 with respect to the urethane/olefin composite substrate 15.

Hereinafter, the method for producing a medical pressure-sensitive adhesive sheet of the second embodiment will be described in detail by appropriately referring to FIGS. 5A to 5E.

1. Process of Forming Urethane/Olefin Composite Substrate

Figure 5A:
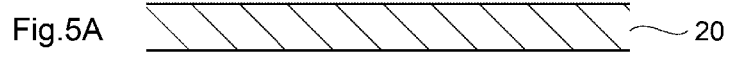
FIGS. 5A to 5E are diagrams presented to illustrate a method for producing a medical pressure-sensitive adhesive sheet.

First, a process sheet 20 is prepared as illustrated in FIG. 5A.

Figure 5B:
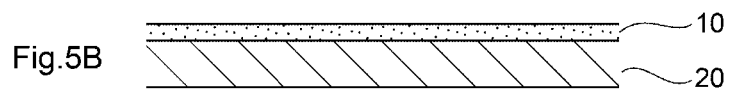

Next, a predetermined urethane substrate 10 is formed on the process sheet 20 as illustrated in FIG. 5B.

In other words, it is possible to form a urethane substrate which consists of a predetermined urethane resin and has a predetermined thickness by coating the urethane resin raw material (the isocyanate compound and the polyhydric alcohol compound) described above on the release sheet using a roll coater or the like and heat-treating the resultant using an oven to perform the dehydration reaction thereof.

Figure 5C:
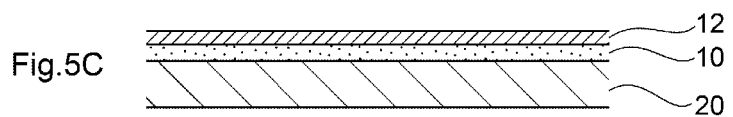

Next, as illustrated in FIG. 5C, the interlayer adhesive layer 12 having a predetermined thickness is formed on the urethane substrate 10 having a predetermined thickness.

In other words, it is possible to form the interlayer adhesive layer consisting of a predetermined urethane-based adhesive or the like by coating an acrylic pressure-sensitive adhesive containing a crosslinking agent or the like on the urethane substrate having a predetermined thickness and heat-treating the resultant to scatter the solvent and also to perform the partial crosslinkage thereof.

Here, the interlayer adhesive layer may have a single-layer structure constituted with one layer or a multilayer structure constituted with two or more layers.

Hence, it is possible to simplify the manufacturing process and to produce at a low cost as a whole in a case in which the interlayer adhesive layer has a single-layer structure constituted with one layer.

In addition, in a case in which the interlayer adhesive layer has a multilayer structure constituted with two or more layers, any layer of the two or more layers can be formed as an anchor layer containing a silane coupling agent or the like and thus the urethane substrate and the olefin nonwoven fabric can be firmly adhered to each other.

Figure 5D:
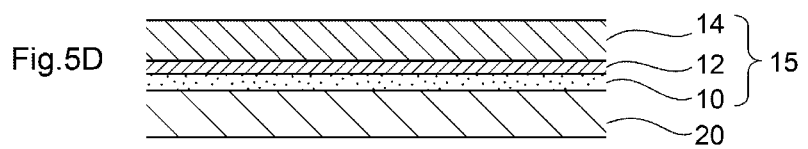

Next, as illustrated in FIG. 5D, it is possible to obtain the urethane/olefin composite substrate 15 by forming a predetermined olefin nonwoven fabric 14 on the interlayer adhesive layer 12 using a laminator roll or the like.

2. Process of Forming Pressure-Sensitive Adhesive Layer for Pasting

Figure 5E:
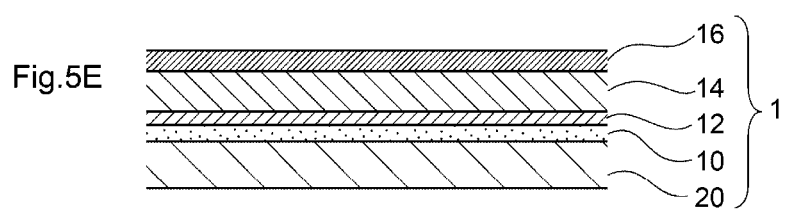
Figure 6A:
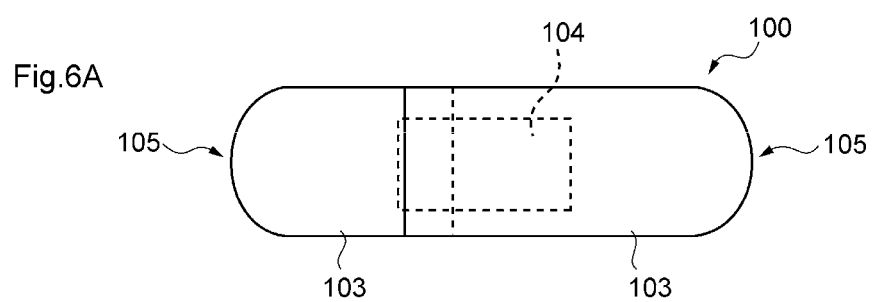
FIGS. 6A and 6B are diagrams presented to illustrate the plan view and cross-sectional view of a pressure-sensitive adhesive film for first-aid adhesive plaster of the related art.
Figure 6B:
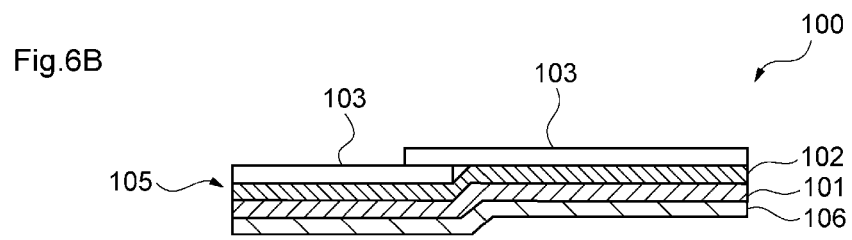

As illustrated in FIG. 5E, the process of forming a pressure-sensitive adhesive layer for pasting is a process to form the pressure-sensitive adhesive layer for pasting 16 with respect to the urethane/olefin composite substrate 15 formed in advance.

Here, the pressure-sensitive adhesive layer for pasting is preferably constituted with an acrylic pressure-sensitive adhesive or an olefin-based adhesive which contains a crosslinking agent, a rubber-based pressure-sensitive adhesive, a silicone pressure-sensitive adhesive or the like.

The acrylic pressure-sensitive adhesive or the olefin-based pressure-sensitive adhesive is a suitable pressure-sensitive adhesive in terms that it also exhibits favorable adhesiveness with respect to the olefin nonwoven fabric as well as it is relatively inexpensive and easily pasted to the skin or the like.

Moreover, the rubber-based pressure-sensitive adhesive is a suitable pressure-sensitive adhesive in terms that it is relatively thin but high adhesive force can be easily obtained.

Furthermore, the silicone pressure-sensitive adhesive is a suitable pressure-sensitive adhesive in terms that it also exhibits favorable adhesiveness with respect to the olefin nonwoven fabric as well as it exhibits favorable tacky property and high biocompatibility or the like.

In addition, the pressure-sensitive adhesive layer for pasting can be formed by directly coating a pressure-sensitive adhesive for pasting with respect to the urethane/olefin composite substrate.

Alternatively, it is also possible to form the pressure-sensitive adhesive layer for pasting indirectly by layering the pressure-sensitive adhesive layer for pasting coated on the paper for release process in advance with respect to the urethane/olefin composite substrate by the so-called transfer method.

In either case, the coating method of the pressure-sensitive adhesive for pasting is not particularly limited, and the pressure-sensitive adhesive layer for pasting can be easily formed by uniformly coating a pressure-sensitive adhesive composition on the substrate using, for example, a roll coater, a comma coater, a knife coater, ink jet, screen printing or the like as a coating apparatus.

Furthermore, it is preferable to scatter the solvent, to perform a crosslinking treatment, or further to perform a seasoning treatment under a certain condition in order to promote the crosslinking reaction during the process of forming the pressure-sensitive adhesive layer for pasting although it depends on the kind of the pressure-sensitive adhesive for pasting.

3. Process of Layering Release Sheet

Next, the process of layering a release sheet of the medical pressure-sensitive adhesive sheet is a process to further layer a release sheet on the pressure-sensitive adhesive layer for pasting although it is not illustrated in the drawing.

In this case also, the method for layering the release sheet is not particularly limited, and, for example, a laminating apparatus or a pressing roll can be suitably used.

4. Process of Cutting Medical Pressure-Sensitive Adhesive Sheet

Next, the process of cutting a medical pressure-sensitive adhesive sheet is a process to obtain a medical pressure-sensitive adhesive sheet having a predetermined shape by pressing the layered product in a state in which the urethane substrate is layered between the cutting tool and the cradle and cutting into a predetermined shape although it is also not illustrated in the drawing.

In this case, a cutter, a knife, a laser, a cutting frame or the like can be used as the cutting tool.

EXAMPLES

Hereinafter, the invention will be described in more detail with reference to Examples.

Example 1

1. Production of Medical Pressure-Sensitive Adhesive Sheet

A urethane-based resin was coated on the first release sheet using a roll coater and heat-treated so as to form a urethane substrate having a thickness of 5 μm, a maximum point elongation percentage measured in conformity with JIS K 7127 of 800%, and a moisture permeability amount measured in conformity with JIS Z 0208 of 4000 g/(m$^2$·24 hours).

Next, a urethane-based adhesive (in semi-cured state) was coated on the urethane substrate thus formed using a roll coater at a thickness of 12 μm.

Subsequently, an olefin nonwoven fabric (mass per unit area: 40 g/m$^2$, 100% modulus (longitudinal direction): 4 N/50 mm, maximum point strength (longitudinal direction and transverse direction): 8.5 N/50 mm and 7.2 N/50 mm, maximum point elongation percentage (longitudinal direction and transverse direction): 586% and 520%) produced using only a polypropylene-based thermoplastic elastomer (100% by weight) as the raw material by the melt blow method was layered on the urethane-based adhesive (in semi-cured state) having a thickness of 12 μm using a laminator.

In other words, the pressure treatment was performed using a pressure roll of the laminator under the conditions of 25° C., 20 N/cm, and a line speed of 10 m/min so as to obtain a urethane/olefin composite substrate with release sheet having a thickness of 100 μm.

Subsequently, an acrylic pressure-sensitive adhesive containing an isocyanate-based crosslinking agent was coated on the urethane/olefin composite substrate thus obtained using a roll coater and heat-treated so as to form an acrylic pressure-sensitive adhesive layer having a thickness of 20 μm.

Subsequently, the second release sheet was layered with respect to the urethane/olefin composite substrate equipped with the acrylic pressure-sensitive adhesive layer thus formed using a laminator, and then the resultant was subjected to the aging treatment under the condition of 60° C. and 168 hours, thereby obtaining a medical pressure-sensitive adhesive sheet of Example 1.

Meanwhile, the urethane substrate, the interlayer adhesive, the olefin nonwoven fabric, and the pressure-sensitive adhesive for pasting which constitute the medical pressure-sensitive adhesive sheet of Example 1 are denoted as UTYP1, ATYP1, OTYP1, and TTYP1, respectively, and described in Table 1.

2. Evaluation of Medical Pressure-Sensitive Adhesive Sheet (1) Elongation Percentage (Evaluation 1)

The medical pressure-sensitive adhesive sheet thus obtained was cut into a predetermined size (length: 100 mm, width: 50 mm), and then the maximum point elongation percentage (longitudinal direction and transverse direction) of the medical pressure-sensitive adhesive sheet was measured in conformity with JIS Z 0237, and the elongation percentage was evaluated according to the following criteria. The results thus obtained are presented in Table 2.

Very Good: Elongation percentage is a value of 350% or more in the longitudinal direction and the transverse direction, respectively.

Good: Elongation percentage is a value of 300% or more in the longitudinal direction and the transverse direction, respectively.

Fair: Elongation percentage is a value of 200% or more in the longitudinal direction and the transverse direction, respectively.

Bad: Elongation percentage is a value of below 200% in the longitudinal direction and the transverse direction, respectively.

(2) 100% Modulus (Evaluation 2)

The medical pressure-sensitive adhesive sheet thus obtained was cut into a predetermined size (length: 100 mm, width: 50 mm), and then the 100% modulus (longitudinal direction and the transverse direction) of the medical pressure-sensitive adhesive sheet was measured in conformity with JIS Z 0237, and the rupture property was evaluated according to the following criteria. The results thus obtained are presented in Table 2.

Very Good: It is a value within the range of from 8 to 15 N/50 mm.

Good: It is out of the above range and a value within the range of from 5 to 20 N/50 mm.

Fair: It is out of the above range and a value within the range of from 3 to 30 N/50 mm.

Bad: It is a value of below 3 N/50 mm or above 30 N/50 mm.

(3) Moisture Permeability Amount (Evaluation 3)

The medical pressure-sensitive adhesive sheet thus obtained was cut into a predetermined size (length: 100 mm, width: 100 mm), and then the moisture permeability amount of the medical pressure-sensitive adhesive sheet was measured in conformity with JIS Z 0208 and evaluated according to the following criteria. The results thus obtained are presented in Table 2.
Very Good: Moisture permeability amount is a value of 3000 g/(m²·24 hours) or more.
Good: Moisture permeability amount is a value of 2000 g/(m²·24 hours) or more.
Fair: Moisture permeability amount is a value of 1500 g/(m²·24 hours) or more.
Bad: Moisture permeability amount is a value of below 1500 g/(m²·24 hours).

(4) Water Bearing Pressure (Evaluation 4)

The medical pressure-sensitive adhesive sheet thus obtained was cut into a predetermined size (length: 100 mm, width: 100 mm) and then the water bearing pressure of the medical pressure-sensitive adhesive sheet was measured in conformity with the method B (high water pressure method) of JIS L 1092 and evaluated according to the following criteria. The results thus obtained are presented in Table 2.
Very Good: Water bearing pressure is a value of 1000 mm H₂O or more.
Good: Water bearing pressure is a value of 800 mm H₂O or more.
Fair: Water bearing pressure is a value of 500 mm H₂O or more.
Bad: Water bearing pressure is a value of below 500 mm H₂O.

(5) Stickiness (Evaluation 5)

The medical pressure-sensitive adhesive sheet thus obtained was cut into a predetermined size (length: 150 mm, width: 25 mm) and then the stickiness of the medical pressure-sensitive adhesive sheet was measured as the peel force (peel strength) at the time of peeling off in 180° direction with respect to a stainless steel plate in conformity with JIS Z 0237 and evaluated according to the following criteria. The results thus obtained are presented in Table 2.
Very Good: Peel force is a value of 6 N/25 mm or more.
Good: Peel force is a value of 4 N/25 mm or more.
Fair: Peel force is a value of 2 N/25 mm or more.
Bad: Peel force is a value of below 2 N/25 mm.

(6) Handleability (Evaluation 6)

The medical pressure-sensitive adhesive sheet thus obtained was cut into a predetermined size (length: 100 mm, width: 10 mm), and then the first release sheet and the second release sheet were peeled off therefrom and the resultant was pasted to a glass plate having a thickness of 10 mm, the time until finishing pasting the resultant was measured, and the handleability of the medical pressure-sensitive adhesive sheet was evaluated according to the following criteria. The results thus obtained are presented in Table 2.
Very Good: It can be pasted within 30 seconds.
Good: It can be pasted within 60 seconds.
Fair: It can be pasted within 120 seconds.
Bad: It cannot be pasted within 120 seconds.

Examples 2 and 3

In Examples 2 and 3, the medical pressure-sensitive adhesive sheet was produced in the same manner as in Example 1 except changing the thickness of the urethane substrate to the value presented in Table 1 and evaluated.

In other words, in Example 2, the medical pressure-sensitive adhesive sheet was produced in the same manner as in Example 1 except changing the thickness of the urethane substrate to 8 μm and evaluated. Meanwhile, the results thus obtained are presented in Table 2 as well as the urethane substrate used in Example 2 is denoted as UTYP2 and described in Table 1.

In addition, in Example 3, the medical pressure-sensitive adhesive sheet was produced in the same manner as in Example 1 except changing the thickness of the urethane substrate to 10 μm and evaluated. Meanwhile, the results thus obtained are presented in Table 2 as well as the urethane substrate used in Example 3 is denoted as UTYP3 and described in Table 1.

Examples 4 and 5

In Examples 4 and 5, the medical pressure-sensitive adhesive sheet was produced in the same manner as in Example 1 except changing the maximum point elongation percentage of the olefin nonwoven fabric and evaluated.

In other words, in Example 4, the medical pressure-sensitive adhesive sheet was produced in the same manner as in Example 1 except that the maximum point elongation percentage (longitudinal direction and transverse direction) of the olefin nonwoven fabric produced by the melt blow method using a mixture (weight ratio=75% by weight/25% by weight) of a polypropylene-based thermoplastic elastomer and a polypropylene resin or the like as the raw materials of the olefin nonwoven fabric was set to 430% and 370%, respectively, and evaluated. Meanwhile, the results thus obtained are presented in Table 2 as well as the olefin nonwoven fabric used in Example 4 is denoted as OTYP2 and described in Table 1.

In addition, in Example 5, the medical pressure-sensitive adhesive sheet was produced in the same manner as in Example 1 except that the maximum point elongation percentage (longitudinal direction and transverse direction) of the olefin nonwoven fabric produced by the spunbond method using a mixture (weight ratio=75% by weight/25% by weight) of a polypropylene-based thermoplastic elastomer and a polypropylene resin or the like as the raw materials of the olefin nonwoven fabric was set to about 270% and about 340%, respectively, and evaluated. Meanwhile, the results thus obtained are presented in Table 2 as well as the olefin nonwoven fabric used in Example 5 is denoted as OTYP3 and described in Table 1.

Comparative Examples 1 to 3

In Comparative Examples 1 to 3, the medical pressure-sensitive adhesive sheet was produced in the same manner as in Example 1 except that the thickness of the urethane substrate, the thickness of the interlayer adhesive of the urethane substrate, the maximum elongation percentage of the olefin nonwoven fabric, and the thickness of the pressure-sensitive adhesive layer for pasting were set to the values out of the range of the invention, and evaluated.

In other words, in Comparative Example 1, the medical pressure-sensitive adhesive sheet was produced in the same manner as in Example 1 except changing the thickness of the urethane substrate from 10 μm to 30 μm and evaluated. Meanwhile, the results thus obtained are presented in Table 2 as well as the urethane substrate used in Comparative Example 1 is denoted as UTYP4 and described in Table 1.

In addition, in Comparative Example 2, the medical pressure-sensitive adhesive sheet was produced in the same manner as in Example 1 except that the raw material of the olefin nonwoven fabric was changed and the maximum elongation percentage (longitudinal direction and transverse direction) was set to 180% or less in each direction, and evaluated. Meanwhile, the results thus obtained are presented in Table 2 as well as the olefin nonwoven fabric used in Comparative Example 2 is denoted as OTYP4 and described in Table 1.

In addition, in Comparative Example 3, the medical pressure-sensitive adhesive sheet was produced in the same manner as in Example 1 except that the thickness of the interlayer adhesive was changed from 12 μm to 50 μm and the thickness of the pressure-sensitive adhesive layer for pasting was set to 100 μm, and evaluated. Meanwhile, the results thus obtained are presented in Table 2 as well as the interlayer adhesive and the pressure-sensitive adhesive for pasting used in Comparative Example 3 are denoted as ATYP2 and TTYP2, respectively, and described in Table 1.

TABLE 1

|  | Urethane substrate | Interlayer adhesive | Olefin nonwoven fabric | Pressure-sensitive adhesive for pasting |
|---|---|---|---|---|
| Example 1 | UTYP1 | ATYP1 | OTYP1 | TTYP1 |
| Example 2 | UTYP2 | ATYP1 | OTYP1 | TTYP1 |
| Example 3 | UTYP3 | ATYP1 | OTYP1 | TTYP1 |
| Example 4 | UTYP1 | ATYP1 | OTYP2 | TTYP1 |
| Example 5 | UTYP1 | ATYP1 | OTYP3 | TTYP1 |
| Comparative Example 1 | UTYP4 | ATYP1 | OTYP1 | TTYP1 |
| Comparative Example 2 | UTYP1 | ATYP1 | OTYP4 | TTYP1 |
| Comparative Example 3 | UTYP1 | ATYP2 | OTYP1 | TTYP2 |

TABLE 2

|  | Evaluation 1 (extensibility) | Evaluation 2 (modulus) | Evaluation 3 (moisture permeability amount) | Evaluation 4 (water bearing pressure) | Evaluation 5 (stickiness) | Evaluation 6 (handleability) |
|---|---|---|---|---|---|---|
| Example 1 | Very Good | Very Good | Very Good | Very Good | Very Good | Good |
| Example 2 | Very Good | Very Good | Very Good | Very Good | Very Good | Very Good |
| Example 3 | Good | Good | Good | Very Good | Very Good | Very Good |
| Example 4 | Good | Good | Very Good | Very Good | Very Good | Good |
| Example 5 | Fair | Fair | Very Good | Very Good | Very Good | Good |
| Comparative Example 1 | Fair | Fair | Bad | Very Good | Very Good | Very Good |
| Comparative Example 2 | Bad | Bad | Very Good | Very Good | Very Good | Very Good |
| Comparative Example 3 | Bad | Bad | Bad | Very Good | Very Good | Very Good |

INDUSTRIAL APPLICABILITY

According to the medical pressure-sensitive adhesive sheet of the invention, it is possible to significantly improve the elasticity or handleability of the medical pressure-sensitive adhesive sheet while maintaining excellent moisture permeability or water resistance by constituting the medical pressure-sensitive adhesive sheet in which a ultrathin urethane substrate, an interlayer adhesive layer, a predetermined olefin nonwoven fabric, and a pressure-sensitive adhesive layer for pasting are layered in order from the bottom.

In addition, according to the method for producing a medical pressure-sensitive adhesive sheet of the invention, it is possible to efficiently produce a medical pressure-sensitive adhesive sheet exhibiting significantly improved elasticity or handleability while maintaining excellent moisture permeability or water resistance.

Consequently, it is possible to obtain significantly favorable sense of use or handleability even in the case of constituting an adhesive plaster or the like as a medical pressure-sensitive adhesive sheet.

What is claimed is:

1. A medical pressure-sensitive adhesive sheet comprising a urethane substrate, an interlayer adhesive layer, an olefin nonwoven fabric, and a pressure-sensitive adhesive layer for pasting in order and having a moisture permeability amount of 2000 g/(m$^2$·24 hours) or more, wherein a thickness of the urethane substrate is a value within the range of from 1 to 10 μm, the interlayer adhesive layer is a urethane-based adhesive layer, a thickness of the interlayer adhesive layer is a value within the range of from 5 to 30 μm, the olefin nonwoven fabric is constituted with a polypropylene-based thermoplastic elastomer and has a maximum point elongation percentage of a value of 200% or more in a longitudinal direction and a transverse direction, respectively, a content of the polypropylene-based thermoplastic elastomer contained in the olefin nonwoven fabric is a value of above 95% by weight with respect to a total amount of raw materials of the olefin nonwoven fabric, an MFR of the polypropylene-based thermoplastic elastomer contained in the olefin nonwoven fabric is a value within the range of from 1 to 48 g/10 minutes (temperature: 230° C.), and a thickness of the pressure-sensitive adhesive layer for pasting is a value within the range of from 5 to 45 μm.

2. The medical pressure-sensitive adhesive sheet according to claim 1, wherein a mass per unit area of the olefin nonwoven fabric is a value within the range of from 10 to 100 g/m$^2$.

3. The medical pressure-sensitive adhesive sheet according to claim 1, wherein a 100% modulus of the olefin nonwoven fabric is a value within the range of from 2 to 30 N/50 mm.

4. The medical pressure-sensitive adhesive sheet according to claim 1, wherein a 100% modulus of a urethane/olefin composite substrate consisting of the urethane substrate/interlayer adhesive layer/olefin nonwoven fabric is a value within the range of from 3 to 30 N/50 mm.

5. The medical pressure-sensitive adhesive sheet according to claim 1, wherein a peel strength between the urethane substrate and the olefin nonwoven fabric is a value within the range of from 2 to 20 N/50 mm.

6. The medical pressure-sensitive adhesive sheet according to claim 1, wherein the urethane-based adhesive layer is formed from a combination of a polyol compound and an isocyanate curing agent.

7. A method for producing a medical pressure-sensitive adhesive sheet including a urethane substrate having a thickness of from 1 to 10 μm, an interlayer adhesive layer having a thickness of from 5 to 30 μm, an olefin nonwoven fabric constituted with a polypropylene-based thermoplastic elastomer and having a maximum point elongation percentage of a value of 200% or more in a longitudinal direction and a transverse direction, respectively, and a pressure-sensitive adhesive layer for pasting having a thickness of from 5 to 45 μm in order and having a moisture permeability amount of 2000 g/(m$^2$·24 hours) or more, the method comprising the following processes (1) and (2):

(1) a process of layering the urethane substrate and the olefin nonwoven fabric via the interlayer adhesive layer to form a urethane/olefin composite substrate; and (2) a process of forming the pressure-sensitive adhesive layer for pasting with respect to the urethane/olefin composite substrate.

8. The method for producing a medical pressure-sensitive adhesive sheet according to claim 7, wherein the interlayer adhesive layer is a urethane-based adhesive layer.

9. The method for producing a medical pressure-sensitive adhesive sheet according to claim 7, wherein a content of the polypropylene-based thermoplastic elastomer contained in the olefin nonwoven fabric is a value of above 95% by weight with respect to a total amount of raw materials of the olefin nonwoven fabric.

10. The method for producing a medical pressure-sensitive adhesive sheet according to claim 7, wherein an MFR of the polypropylene-based thermoplastic elastomer contained in the olefin nonwoven fabric is a value within the range of from 1 to 48 g/10 minutes (temperature: 230° C.).

\* \* \* \* \*